United States Patent [19]

Staniek et al.

[11] Patent Number: 6,103,796
[45] Date of Patent: Aug. 15, 2000

[54] PROCESSING STABILIZER COMPOSITION

[75] Inventors: Peter Staniek, Kandern; Klaus Stoll, Ruemmingen, both of Germany; Rainer Wolf, Allschwil, Switzerland

[73] Assignee: Clariant Finance (BVI) Limited, Tortola, Virgin Islands (Br.)

[21] Appl. No.: 08/943,876

[22] Filed: Oct. 3, 1997

Related U.S. Application Data

[63] Continuation of application No. 08/248,282, May 23, 1994, abandoned.

[30] Foreign Application Priority Data

May 24, 1993 [GB] United Kingdom .................... 9310696
Oct. 29, 1993 [GB] United Kingdom .................... 9322323

[51] Int. Cl.$^7$ ................................ C08K 5/34; C08K 5/49; C08K 5/53; C09K 15/32
[52] U.S. Cl. .......................... 524/100; 524/102; 524/117; 524/119; 524/135; 524/153; 252/400.24; 252/400.52
[58] Field of Search ......................... 252/400.24, 400.52; 524/100, 102, 117, 119, 135, 153

[56] References Cited

U.S. PATENT DOCUMENTS

| 4,857,230 | 8/1989 | Matsumara ............................... 252/400 |
| 5,106,898 | 4/1992 | Nosu et al. .............................. 524/313 |
| 5,597,857 | 1/1997 | Thibaut et al. .......................... 524/400 |

*Primary Examiner*—Kriellion S. Morgan
*Attorney, Agent, or Firm*—Hesna J. Pfeiffer; Scott E. Hanf

[57] ABSTRACT

A homogeneous blended additive useful as a processing stabilizer for polymers which is a blend of Component (a), a defined phosphite or phosphonite; and Component (b) which is micronized zinc oxide. Component (b) is preferably in an amount of 5 to 10% based on the weight of component (a). This additive composition improves the resistance of phosphites and phosphonites against hydrolysis in the presence of moisture, by providing Component (b) as a hydrolysis stabilizer for Component (a).

4 Claims, No Drawings

PROCESSING STABILIZER COMPOSITION

This is a continuation of application Ser. No. 08/248,282, filed May 23, 1994 abandoned.

The invention relates to new compositions for stabilizing polymeric materials against degradation which takes place e.g. during processing at high temperatures, during the "natural" aging of polymers in the form of pelletized or non-extruded shaped material or in the form of finished polymer articles or during "artificial" aging such as oven aging tests at elevated temperatures, UV light stability tests or weatherability tests.

Phosphites and phosphonites (for example Sandostab P-EPQ) are well known processing stabilizers for a variety of polymers and have been commercially used for many years. Despite their importance for a wide scope of polymers and their high performance as stabilizers, phosphites and phosphonites have the drawback that they can hydrolyze in the presence of moisture, which adversely affects (i.e. reduces) their storage stability as well as their effectiveness in protecting polymeric materials against degradation.

Hydrolytically decomposed phosphites and phosphonites are far less effective when used as stabilizers and, hence, generally produce undesired impurities into polymers. Hydrolysis of phosphites and phosphonites can even lead to a reverse effect on their stabilizing properties so that degradation of polymers is accelerated.

It is, therefore, of paramount importance not only to safeguard the neat phosphites and phosphonites themselves against hydrolysis during storage but also to inhibit their hydrolytic decomposition in polymers.

It is an important advantage that the phosphonites, when incorporated into polymers, are also protected against the influence of moisture, humidity and water so that the properties of the polymers are not adversely affected.

Furthermore, the progress in the development of polymerisation catalysts and their industrial application, especially in case of supported catalysts for the manufacture of polyolefins, has made a variety of polymers available which differ significantly from "early generation" polymers. The problem of hydrolysis of phosphites and phosphonites has been aggravated especially in polyolefins, produced by Generation II to V catalysts which are not removed from the polymer after the finalized polymerisation reaction. Even though such catalysts can be deactivated by catalysts poisons, such as steam, aliphatic alcohols, ethers or ketones, they still remain active in sufficient residual amounts that they have been found to continue to promote the hydrolysis of phosphites and phosphonites in polymers. These adverse effects can be caused by cations with a charge $\geq 2+$, e.g. Mg(2+), Ca(2+), B(3+), Al(3+) and particularly the transition metal ions of the 3d, 4d and 5d series, such as titanium, chromium or zirconium. The residual activity of such deactivated residues of polymerisation catalysts is still sufficient to catalyze the hydrolysis of processing stabilizers. It has now been found that the new compositions according to the invention used for stabilizing polymeric materials inhibit any detrimental interaction between processing stabilizers and the aforementioned catalyst residues.

Additionally it must be noted that metal and metal ion impurities in the neat phosphites or phosphonites also act as accelerators for the hydrolysis. Such impurities can be incorporated into the phosphites or phosphonites during their manufacture, e.g. by corrosion or abrasion of metal of the production equipment (vessels, stirrers, grinders, feeding-tubes, etc.) or can be residues of reaction components such as aluminium, iron or zinc residues of Friedel-Crafts reactions that have not been completely removed. It has been found that the negative influence of such impurities, which cannot be completely excluded from industrially manufactured products, can be overcome by the present invention, i.e. the resistance of processing stabilizers like phosphites and phosphonites against hydrolysis is improved by the use of HALS compounds.

The hydrolysis of phosphites and phosphonites finally leads to products with acidic properties and also to undesired free phenol. Such acids formed in the polymer can accelerate the degradation of the polymer chains and can, moreover, cause many disadvantageous side effects. Such negative effects are acute during the processing of polymers at elevated temperatures. It was found that hydrolyzed processing stabilizers can cause, for example, enhanced formation of undesired gel particles, especially in polyethylenes, or can lead to increased amounts of phosphorus containing black specks. It has also been observed that the corrosion of the processing equipment can be accelerated by the acid products of such hydrolysis reactions. Furthermore, hydrolyzed processing stabilizers were found to reduce the effectivity of sterically hindered amine light stabilizers (HALS) as well as the performance of primary phenolic antioxidants relating to the long term stabilization of polymers.

Therefore, there is a real need to improve the resistance of phosphites and phosphonites against hydrolysis. In particular, the need to protect these processing stabilizers especially in polyolefins produced with Generation II to V catalysts (supported catalysts) results directly from the requirement to maintain optimum polymer properties.

Such a series of detrimental consequences due to the hydrolysis of processing stabilizers themselves as well as processing stabilizers containing polymers can be avoided by the present invention.

Therefore, the high performance of phosphites and phosphonites as stabilizers for polymers, especially when used for maintaining melt flow and color stability, can be safeguarded by a composition according to the present invention so that their application under the normal environmental conditions, including moisture and humidity, is significantly improved. Surprisingly has been found that even phosphonites of high hydrolytic sensitivity can be protected according to the invention.

According to the invention there is provided an additive, useful as a processing stabilizer for polymers, the additive comprising a blend (preferably a homogeneous blend) of:
a) one or more phosphonites or phosphites, preferably of formulae I to V (hereinafter defined as component a)

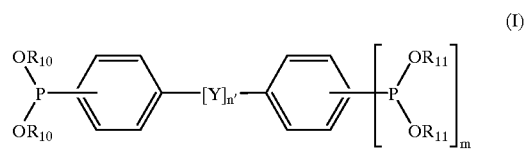

(I)

(II)

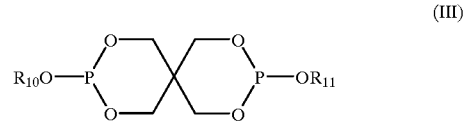

(III)

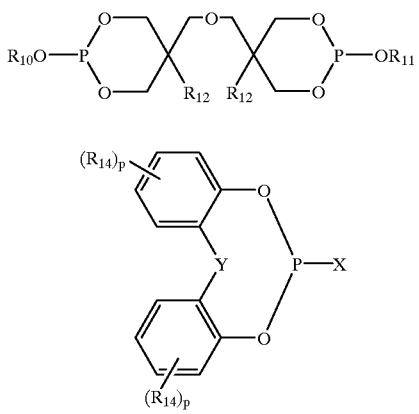

in which
- m is 0 or 1;
- n' is 0 or 1;
- p is 0 to 4, preferably 1 to 3
- each $R_{10}$ and each $R_{11}$, independently, is a group derived from an aliphatic, or alicyclic or aromatic alcohol containing one or two OH groups; whereby the two —OH groups are not positioned to be able to form a P-containing ring; (hereinafter defined as the monovalent significances of $R_{10}$ or $R_{11}$ respectively);
- or both groups $R_{10}$ and/or $R_{11}$ form a group derived from an aliphatic, alicyclic or aromatic alcohol containing two or more OH groups in such a position that they can form a cyclic group with a single phosphorus atom (hereinafter defined as the divalent significances of $R_{10}$ or $R_{11}$ respectively);
- $R_{12}$ is —OH, $CH_2OH$ or $C_{1-4}$alkyl.
- each $R_{14}$ independently is selected from $C_{1-22}$alkyl or $C_{7-22}$aralkyl;
- X is F or —O—$R_{10}$;
- Y is —O—, —S—, —CH($R_{15}$)— or —$C_6H_4$—, where $R_{15}$ is hydrogen or $C_{1-8}$alkyl or $COOR_6$ and $R_6$ is $C_{1-8}$alkyl; with b) a hydrolytic stabilizer selected from compounds containing a sterically hindered amine group (preferably a sterically hindered piperdinyl group) and micronized zinc oxide (hereinafter defined as component b).

In the past the components a) and b) have been added individually to the polymeric compositions. What we have found is that by blending the compounds as a stabilising composition, prior to addition to the polymer, the disadvantages of hydrolytic instability can be avoided.

Further according to the invention there is provided a process, for stabilising a polymeric composition, comprising
i) blending
a) one or more phosphonites or phosphites, preferably of formulae I to V (hereinafter defined as component a)

(I)

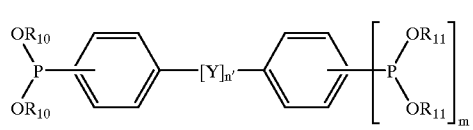

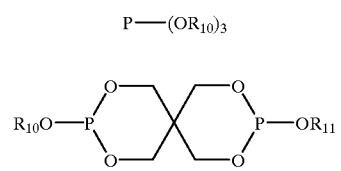

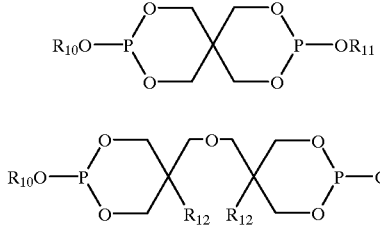

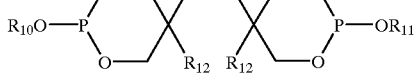

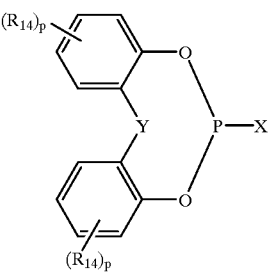

in which
- m is 0 or 1;
- n' is 0 or 1;
- p is 0 to 4, preferably 1 to 3
- each $R_{10}$ and each $R_{11}$, independently, is a group derived from an aliphatic, or alicyclic or aromatic alcohol containing one or two OH groups; whereby the two —OH groups are not positioned to be able to form a P-containing ring; (hereinafter defined as the monovalent significances of $R_{10}$ or $R_{11}$ respectively);
- or both groups $R_{10}$ and/or $R_{11}$ form a group derived from an aliphatic, alicyclic or aromatic alcohol containing two or more OH groups in such a position that they can form a cyclic group with a single phosphorus atom (hereinafter defined as the divalent significances of $R_{10}$ or $R_{11}$ respectively);
- $R_{12}$ is —OH, $CH_2OH$ or $C_{1-4}$alkyl.
- each $R_{14}$ independently is selected from $C_{1-22}$alkyl or $C_{7-22}$aralkyl;
- X is F or —O—$R_{10}$;
- Y is —O—, —S—, —CH($R_{15}$)— or —$C_6H_4$—, where $R_{15}$ is hydrogen or $C_{1-8}$alkyl or $COOR_6$ and $R_6$ is $C_{1-8}$alkyl; with b) a hydrolytic stabilizer selected from compounds containing a sterically hindered amine group (preferably a sterically hindered piperdinyl group) and micronized zinc oxide (hereinafter defined as component b);
followed by
ii) adding this blend to the polymeric material.

Preferably the amount of component b) per 100 parts of component a) is 0.05–15 parts.

Preferably in component a) the monovalent significances of $R_{10}$ and $R_{11}$ are independently derived from linear branched or cyclic $C_{1-24}$ aliphatic alcohols; or phenols, preferably substituted by 1 to 5 groups selected from $C_{1-12}$ alkyl and $C_{7-22}$ aralkyl groups.

Preferably the divalent significances of $R_{10}$ and $R_{11}$ (which are derived from bisphenols) are of the formula

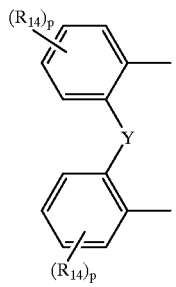

where each $R_{14}$ independently is selected from $C_{1-22}$alkyl or $C_{7-22}$aralkyl.

Further according to the invention there is provided the use of a compound containing a 2,2,6,6-tetramethyl piperidinyl group as a hydrolysis stabilizer for phosphorus compounds for example phosphonites and/or phosphites preferably of formulae I to V in polymeric compositions.

Preferably according to the invention, there is provided an additive, useful as a processing stabilizer for polymers, the additive comprising a blend (preferably a homogeneous blend) of a) one or more phosphonites or phosphites, preferably of formulae I to V defined above (component a) with b) a hydrolytic stabilizer selected from compounds containing a sterically hindered amine group (preferably a sterically hindered piperdinyl group)

Preferably when component b) is selected from compounds containing a sterically hindered amine group (preferably a sterically hindered piperdinyl group) the sterically hindered amine group is of the formula α)

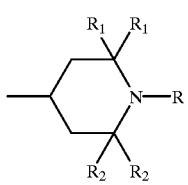

in which

R is hydrogen; oxygen; —OH; $C_{1-24}$alkyl; —O—$C_{1-24}$alkyl; —O—CO—$C_{1-24}$alkyl; —O—CO-phenyl or —$COR_5$; where $R_5$ is —$C(R_3)$=$CH_2$, $C_{1-12}$alkyl, phenyl, CO—$C_{1-24}$alkyl, —CO-phenyl, —$NR_7R_8$, —$CH_2$—$C_6H_5$, —CO—O$C_{1-12}$alkyl or —COOH; $R_3$ is hydrogen or $C_{1-4}$alkyl; $R_7$ is hydrogen, $C_{1-12}$alkyl, $C_{5-6}$cycloalkyl, phenyl, phenyl-$C_{1-4}$alkyl or $C_{1-12}$alkylphenyl and $R_8$ is $C_{1-12}$alkyl or hydrogen, each $R_1$, independently, is —$CH_3$ or —$CH_2(C_{1-4}$alkyl) or both groups $R_1$ form a group —$(CH_2)_5$—; and each $R_2$, independently, is —$CH_3$ or —$CH_2(C_{1-4}$alkyl) or both groups $R_2$ from a group —$(CH_2)_5$—.

Such a group of formula α) is known as a Hindered Amine Light Stabilizer (HALS).

More preferably when component b) is a sterically hindered amine, it is selected from a compound containing a group of formula α'

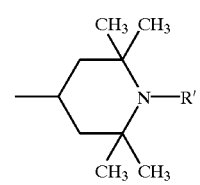

where R' is hydrogen, O, OH, $C_{1-12}$alkyl, $C_{1-12}$alkoxy or —CO—$C_{1-8}$alkyl.

Preferred compounds containing a sterically hindered amine group of component b are selected from HALS 1–HALS 17 below

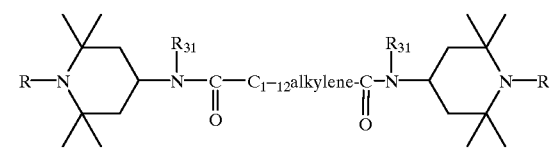

HALS 1

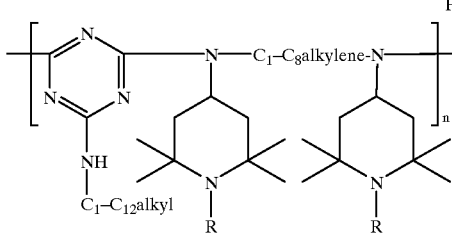

HALS 2 where $R_{31}$ is hydrogen or $C_{1-8}$ alkyl

HALS 3

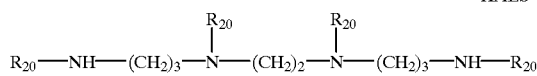

HALS 4

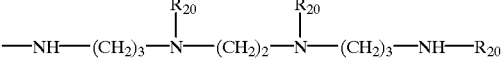

where $R_{20}$ is

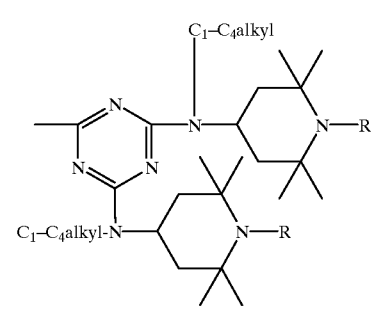

HALS 5
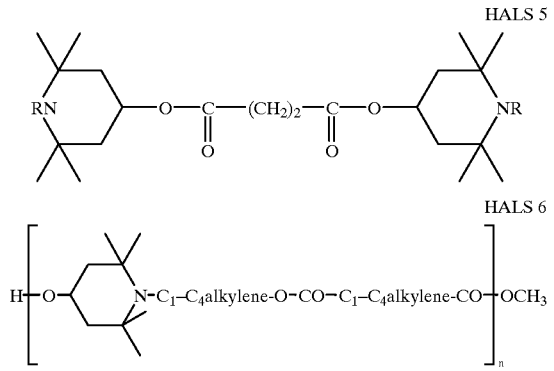
HALS 6
HALS 7
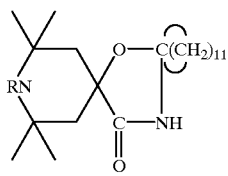
HALS 8
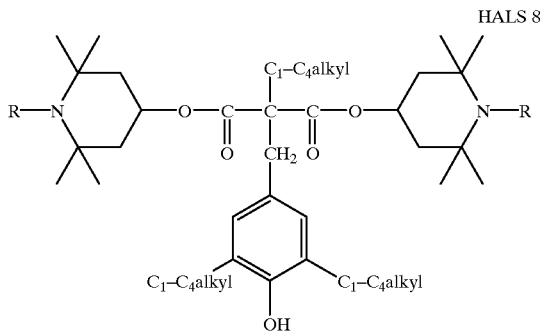
HALS 9
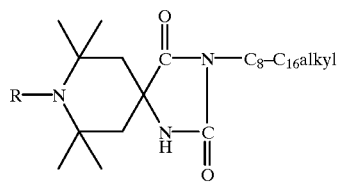
HALS 10
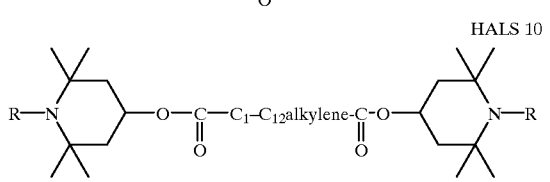
HALS 11
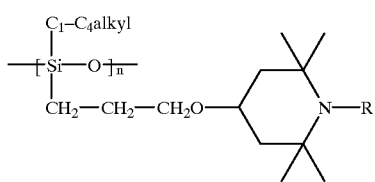
HALS 12
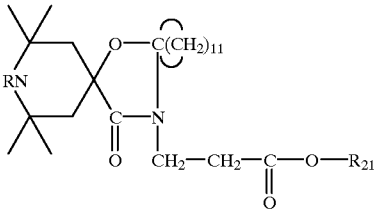
where $R_{21}$ is $C_{12-14}$alkyl (e.g. a mixture of $C_{12}H_{25}$ and $C_{14}H_{29}$);
HALS 13
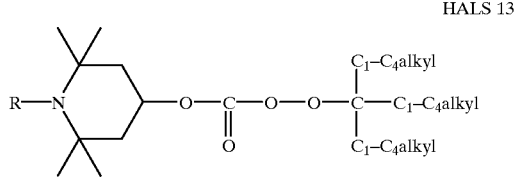
HALS 14
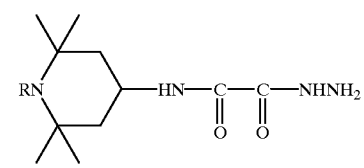
HALS 15
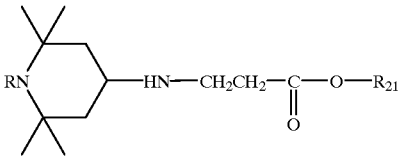
where $R_{21}$ is as defined above
HALS 16
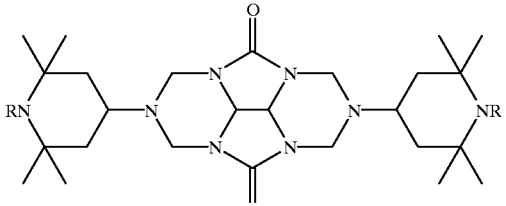
HALS 17
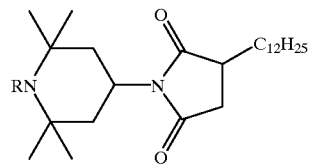

in which in HALS 1 to HALS 17
R is R' where R' is hydrogen, O, OH, $C_{1-12}$alkyl, $C_{1-12}$alkoxy or —CO—$C_{1-8}$alkyl and n is a number from 3 to 20.

Most preferred compounds containing a sterically hindered amine group are as follows:

Bis(2,2,6,6-tetramethyl-4-piperidyl) sebacate;
Bis(1,2,2,6,6-pentamethyl-4-piperidinyl)(3,5-ditert.butyl-4-hydroxybenzyl)butylpropane dioate;
Bis(1,2,2,6,6-pentamethyl-4-piperidinyl) sebacate;
8-Acetyl-3-dodecyl-7,7,9,9-tetramethyl-1,3,8-triazaspiro(4,5)decane-2,4-dione;
Butanedioic acid, bis(2,2,6,6-tetramethyl-4-piperidinyl) ester;
Tetrakis (2,2,6,6-tetramethyl-4-piperidyl)-1,2,3,4-butane tetracarboxylate;
(2,2,6,6-tetramethyl-4-piperidyl/β,β,β',β'-tetramethyl-3,9-(2,4,8,10-tetraoxaspiro(5'5)undecane) diethyl)-1,2,3,4-butane tetra carboxylate;
7-oxa-3,20-diazadispiro(5.1.11.2)heneicosan-20-propanoicacid,2,2,4,4-tetra-methyl-21-oxo, dodecylester ("Hostavin" N 24);
Octadecene-(N-(2,2,6,6-tetramethylpiperidinyl-4-N-maleinimido-oxalic acid diamide copolymer;
N-(2,2,6,6-tetramethyl-4-piperidinyl)-N'-amino-oxamide;
OO-t-amyl-O-(1,2,2,6,6-pentamethyl-4-piperidinyl) monoperoxicarbonate;
β-Alanine, N-(2,2,6,6-tetramethyl-4-piperidinyl), dodecylester;
Ethanediamide,N-(1-acetyl-2,2,6,6-tetramethylpiperidinyl)-N'-dodecyl;
3-dodecyl-1-(2,2,6,6-tetramethyl-4-piperidinyl)-pyrrolidin-2,5-dione;
3-dodecyl-1-(1,2,2,6,6-pentamethyl-4-piperidinyl)-pyrrolidin-2,5-dione;
3-dodecyl-1-(1-acetyl,2,2,6,6-tetramethyl-4-piperidinyl)-pyrrolidin-2,5-dione; ("Sanduvor" 3058)
4-benzoyloxy-2,2,6,6-tetramethylpiperidine;
1-[2-(3,5-di-tert.butyl-4-hydroxyphenylpropionyloxy) ethyl]-4-(3,5-ditert.-butyl-4-hydroxyphenyl-propionyloxy)-2,2,6,6-tetramethyl piperidine;
2-methyl-2-(2",2",6",6"-tetramethyl-4"-piperidinylamino)-N-(2',2',6',6'-tetra-methyl-4'-piperidinyl) propionylamide;
1,2-bis(3,3,5,5-tetramethyl-2-oxo-piperazinyl)ethane-1-isopropyl-3,3,5,5-tetramethyl-2-piperazinone
Tetrakis (2,2,6,6-tetramethyl-4-piperidyl) 1,2,3,4-butane tetracarboxylate;
4-oleoyloxy-2,2,6,6-tetramethylpiperidine;
Poly-[(6-morpholino-s-triazin-2,4-diyl)[(2,2,6,6-tetramethyl-4-piperidinyl)imino]hexamethylene-[(2,2,6,6-tetramethyl-4-piperidinyl)imino)];
Poly-[6-[1,1,3,3-tetramethyl-butyl)imino]-s-triazin-2,4-diyl)[2-(2,2,6,6-tetramethyl-4-piperidinyl)imino] hexamethylene-[4-(2,2,6,6-tetramethyl-4-piperidinyl) imino)];
1,3,5-triazine-2,4,6-triamine-N',N"-[ethanediyl-bis[[[4,6-bis[butyl(1,2,2,6,6-pentamethyl-4-piperidinyl)amine]-1,3,5-triazin-2-yl]imino]propane-diyl]]bis[N',N"-dibutyl-N',N"-bis-(1,2,2,6,6-pentamethyl-4-piperidinyl)];
Butanedioic acid, polymer with 4-hydroxy-2,2,6,6-tetramethyl-1-piperidine-ethanol;
2,2,4,4-tetramethyl-7-oxa-3,20-diaza-dispiro[5.1.11.2] heneicosan-21-one;
Bis(1-octyloxy-2,2,6,6-tetramethyl-4-piperidinyl)sebacate;
Poly(methylpropyl-3-oxy-[2,2,6,6-tetramethyl-4-piperidinyl]-siloxane);
1,3,5,7,9,11-hexaaza-4,10-dione-tricyclo[12.1.1.0$^{13,14}$]-tetradecane-1,7-bis(2,2,6,6-tetramethyl-4-piperidinyl).

Preferably the amount of component b (when a compound containing a sterically hindered amine group) present is 3–10% more preferably 3–5%.

Alternatively preferred is an additive, useful as a processing stabilizer for polymers, the additive comprising a blend (preferably a homogeneous blend) of
a) one or more phosphonites or phosphites, preferably of formula I to V defined above (component a) with
b) micronized zinc oxide (component b), Preferably what is meant by micronized zinc oxide is that the particle size of zinc oxide is below 1 $\mu$m, preferably 0.05–1 $\mu$m.

Preferably, when component b) is zinc oxide, the amount of zinc oxide present is 5–10%, more preferably 6–8%, most preferably 7% based on the weight of component a).

Further according to the invention there is provided the use of zinc oxide (preferably micronized) as a hydrolysis stabilizer for phosphorus compounds, such as phosphonites and/or phosphites, preferably of formula I to V in polymeric compositions.

Still further according to the invention, there is provided a polymeric composition comprising a polymeric material and an additive according to the invention.

Preferably the amount of additive present is 0.01–5%, more preferably 0.1–2% based on the amount of polymeric material to be stabilized.

Polymeric materials that can be stabilized by a stabilizing composition according to the invention include homopolymers, copolymers and polymer blends of:
Cellulose acetate; Cellulose acetobutyrate; Cellulose acetopropionate; Cresol-formaldehyde resins; Carboxymethylcellulose; Cellulose nitrate; Cellulose propionate; Casein plastics; Casein-formaldehyde resins; Cellulose triacetate; Ethyl cellulose; Epoxy resins; Methyl cellulose; Melamineformaldehyde resins; Polyamide; Polyamidimide; Polyacrylonitrile; Polybutene-1 and -2; Polybutylacrylate; Poly(butyleneterephthalate); Polycarbonate; Poly(chloro-trifluoro-ethylene); Poly(diallylphthalate); Polyethylene; chlorinated Polyethylene; Polyetherketone; Polyetherimide; Polyethyleneoxide; Polyethersulphone; Poly(ethyleneterephthalate); Polytetrafluoroethylene; Phenolformaldehyde resins; Polyimide; Polyisobutylene; Polyisocyanurate; Polymethacrylimide; Polymethylmethacrylate; Poly(4-methylpentene-1); Poly($\alpha$-methylstyrene); Polyoxy-methylene; Polyacetal; Polypropylene; Polyphenylene-ether; Polyphenylene-sulphide; Polyphenylenesulphone; Polystyrene; Polysulphone; Polyurethane; Polyvinyl acetate; Polyvinyl alcohol; Polyvinylbutral; chlorinated Polyvinyl chloride; Polyvinylidene chloride; Polyvinylidene fluoride; Polyvinylfluoride; Polyvinylformaldehyde; Polyvinylcarbazole; Polyvinylpyrrolidone; Silicon polymers; saturated polyester; urea-formaldehyde resins; unsaturated polyester; polyacrylates; polymethacrylates; polyacrylamides; maleinate resins; phenolic resins; aniline resins; furane resins; carbamide resins; epoxide resins and silicon resins.

Examples of suitable copolymers include:
Acrylonitrile/butadiene/acrylate; Acrylonitrile/butadiene/styrene; Acrylonitrile/methylmethacrylate; Acrylonitrile/styrene/acrylic ester; Acrylonitrile/ethylenepropylenediene/styrene; Acrylonitrile/chlorinated polyethylene/styrene; Ethylene/ethylacrylate; Ethylene methacrylic acid ester; Ethylene/propylene; Ethylene/propylene-diene; Ethylene/vinyl-acetate; Ethylene/vinyl alcohol; Ethylene/tetrafluoroethylene; Tetrafluoroethylene/hexafluoro-propylene; Methacrylate/butadiene/styrene; Melamine/phenolformaldehyde; Polyester blockamide; Perfluoroalkoxyalkane; Styrene/acrylonitrile; Styrene/butadiene; Styrene/maleic acid anhydride; Styrene/α-methylstyrene; Vinylchloride/ethylene; Vinylchloride/ethylene/methacrylate; Vinylchloride/ethylene/vinyl acetate; Vinylchloride/methyl-methacrylate; Vinylchloride/octylacetate; Vinylchloride/vinylacetate; and Vinylchloride/vinylidene chloride.

Preferred polymeric materials that can be stabilized are polypropylene, polyethylene (e.g. high density polyethylene, low density polyethylene, linear low density polyethylene or medium density polyethylene), polybutylene, poly-4-methylpentene and copolymers thereof as well as polycarbonate, polystyrene and polyurethane.

Preferred polyurethanes are those prepared from isocyanate resins and polyols. Preferred isocyanates are those commercially available as Desmodur, Elastan, Lupranat, Tedimon, Scuranat, Suprasec, Systanat, Hylene, Isonate (-Papi), Multrathane, Nacconate and Sumidur.

Preferred polyols are those commericially available as Desmophen, Lupranol, Lupraphen, Glendion, Napiol, Scuranol, Caradol, Daltolac, Daltorez, Diorez, Estolan, Propylan, Armol, Bermodol, Isonol, Metpol, Multron, Multranol, Niax Polyol, Pluracol, Quadrol, Thanol, Voranol and Sumiphen.

Such polyurethanes are as describes in Saechtling: Kunststoff Taschenbuch 23 Ausgabe—published by Carl Hansen Verlag 1986 (esp. p. 339–410). The contents of this book are incorporated herein by reference.

Preferred powder coatings are described in "The Science of Powder Coatings—Chemistry, Formulation and Application"—David A. Bate published SITA—1990, Vol. 1, the contents of which are incorporated herein by reference, especially pp. 249–277.

The powder coating compositions to which this invention can be applied are any powder coatings known in the art. The powders may be thermoplastic or thermosetting powders and include any known acrylic polyester, epoxy or urethane powder coatings commonly available. Particularly preferred powder coatings are based on acrylate and polyisocyanate resins.

Preferred powder coating are formulations based on epoxy resins for example DER 663 UE, HULS B68, Resiflow PU5, Ceriduol, ACA8, Durcal 10 and Black Regal. Hydroxypolyester resins can be used in polyurethane powder coatings.

Powder lacquers are also described in U.S. Pat. No. 5,036,144, EP 299 420, U.S. Pat. No. 4,937,288 and JP 91-044588, the contents of which are incorporated herein by reference.

Powder coating compositions are more preferably those based on acrylic polymers or isocyanates.

Further additives that can be added to a stabilizing or a polymeric composition according to the invention include antioxidants, such as sterically hindered phenols, secondary aromatic amines or thioethers, such as described in "Kunststoff-Additive"—Gächter/Müller, Ed. 3, 1990 p.42–50, the contents of which are incorporated herein by reference; acid scavengers such as sodium-, magnesium- or calcium- stearates or lactates, hydrotalcite or alkoxylated amines; U.V. stabilizers such as sterically hindered amines (for example N-unsubstituted, N-alkyl or N-acyl substituted 2,2,6,6-tetra-methylpiperidine compounds) [also known as hindered amine light stabilizers—HALS] and U.V. absorbers (e.g. 2-(2'-hydroxyphenyl)-benztriazoles, 2-hydroxybenzophenones, 1,3-bis-(2'-hydroxybenzoyl)benzene salicylates, cinnamates and oxalic acid diamides;), U.V. quenchers such as benzoates and substituted benzoates, antistatic agents, flameproofing agents, lubricants, plasticisers, nucleating agents, metal deactivators, biocides, impact modifiers, fillers, pigments and fungicides.

Stabilizing compositions according to the invention may be added to the polymeric material before, during or after the polymerization step and may be added in solid or molten form, in solution preferably as a liquid concentrate containing from 10 to 80% by weight of the composition and 90 to 20% by weight of solvent or as a solid masterbatch composition containing 10 to 80% (more preferably 40 to 70%) by weight of the composition and 90 to 20% (more preferably 60 to 30%) by weight of a solid polymeric material which is identical with or compatible with the material to be stabilized.

The additive compositions according to the invention may be incorporated by known methods into the polymeric material to be stabilized. Of particular importance is dry-blending of the compositions according to the invention with the polymer or coating shaped polymer particles, e.g. polymer spheres, with the present compositions in the form of a liquid, a solution or a suspension/dispersion. Of particular importance is blending of the compounds with thermoplastic polymers in the melt, for example in a melt blender or during the formation of shaped articles, including films, tubes, fibres and foams by extrusion, injection moulding, blow moulding, spinning or wire coating. The additive compositions according to the invention are particularly useful for polypropylene and polyethylene articles of every type as well as polycarbonate, polystyrene and polyurethane.

The new stabilizer compositions are especially suitable for use in polyolefins and especially α-polyolefins prepared using processing catalysts known as Generation II to Generation V catalysts and which have not been subjected to a catalyst removal step. By the term "catalyst removal step" used herein is meant a step for the purpose of positively removing the catalyst residues contained in the polymerized polyolefins or treating the polyolefins with the compound which can react with the catalyst residue and inactivate or solubilize the residue, such as alcohols or water, and then removing the inactivated or solubilized catalyst residue by physical means such as filtration, washing and centrifuging. Thus, in the case of suspension polymerization, the step of separating the resulting polymer from a dispersion medium, such as a solvent or a liquefied monomer, does not fall under the above-mentioned definition of the catalyst residue removal step, although the catalyst dissolved in the dispersion medium may be removed by a separation step.

The step of adding a small amount of catalyst poisons such as ethers, alcohols, ketones, esters and water to the resulting polymer, to inactivate the catalyst remaining after the completion of polymerization, or the step of treating the resulting polymer suspension with gas such as steam or nitrogen to remove the dispersion medium also does not fall under the above-mentioned definition of the "catalyst residue-removal" step.

What we mean by Generation I catalysts are titanium halide catalysts and an organo aluminium compound or an organo aluminium halide.

What we mean by Generation II catalysts are Generation I catalysts supported on an organo magnesium compound or based on an organo chromium compound supported on $SiO_2$.

lization and Controlled Degradation of Polymers held in Luzern, Switzerland, May 21–23, 1990 in an article on pages 181 to 196 inclusive by Rolf Mülhaupt entitled "New Trends in Polyolefin Catalysts and Influence on Polymer Stability". The contents of this article is incorporated herein by reference and especially Table I on page 184 describing the Generation of Catalysts:

TABLE I

Polyolefin Catalyst Evolution

| Generation Example | Cat. Act. (g/PP/gTi h atm) | % Act. Ti | Stereoreg. | Process Technology (% insol in heptane) |
|---|---|---|---|---|
| I. $TiCl_4/AlR_3$ | 40 | 0.01 | 45% | removal of cat. residues and atactic PP |
| $TiCl_3/AlEt_2Cl$ | 30 | 0.1 | 92% | removal of catalyst residues |
| II $Mg(OEt_2)/TiCl_4/AlR_3$ | 40000 | | 50% | no removal of cat. residues |
| $SiO_2/Cp_2Cr$ | 40000 | HDPE | | (mainly HDPE/IDPE) |
| III Mod. $TiCl_3$cat. | 5000 | 1 | 95% | no purification |
| $MgCl_2/TiCl_4/AlR_3$ -ester donor | 20000 | 10 | 92% | |
| IV $MgCl_2/TiCl_4/AlR_3$ -silane donor | 40000 | 18 | 99% | no purification no extrusion |
| V Bis-indenyl-$TiR_2$ on $(AlCH_3O)_x$ | 40000 | 100 | 99% | novel PPs, narrow MWD |

What we mean by a Generation III catalyst is a Ziegler type complex catalyst supported on a halogen containing magnesium compound.

What we mean by a Generation IV catalyst is a Generation III catalyst with a silane donor.

What we mean by Generation V catalysts is a bis-indenyl organo titanium compound supported on alumoxane or bis cyclopentadienyl titanium halides activated by aluminium alkyl compound.

Further generations of highly specific catalysts, especially useful for manufacturing highly stereoregular poly-α-olefins, which are presently under development, belong in the sense of the present invention also to the aforementioned generations of supported catalyst systems. Examples for the microstructure of such highly stereoregular polyolefins are given by syndiotactic polypropylene, isotactic stereoblock polymers, isotactic polypropylene containing stearic defects randomly distributed along the polymer chain (so called anisotactic polypropylene) or stereoirregular steroblock polymers. Due to the rapid progress in the development of newer generation catalyst systems the commercial significance of these polymers with novel, highly interesting properties increases more and more. However, residues of such further catalyst generations, as long as they contain metals of the 3d, 4d and 5d series of the periodic system supported analogously to the earlier catalyst generations, can also cause disadvantageous properties in the polymer, as long as such residues are still present in the polymer even if in a deactivated form.

Due to this, it can therefore be expected that the new compositions according to the invention are also suitable for overcoming such disadvantageous properties of the polymer. This means that any disadvantageous interaction between processing stabilizers and the aforementioned residues of catalysts of further generations, particularly the hydrolysis of phosphites and phosphonites, is most effectively inhibited.

These generations of catalysts are described in the Twelfth Annual International Conference on Advances in the stabiin which R, in Table 1, is an organo group; HDPE is high density polyethylene, LLDPE is linear low density polyethylene, Cp is cyclopentadienyl, Et is ethyl, PP is polypropylene, MWD is molecular weight distribution and x is an integer above 2 (preferably 2–100).

Further, in this specification, where a range is given, the figures defining the range are included therein. Any group capable of being linear or branched is linear or branched unless indicated to the contrary.

For the avoidance of doubt, in this specification t-butyl means tertiary butyl, $(-C(CH_3)_3)$.

The invention will now be illustrated by the following Examples.

EXAMPLE 1

This example shows that the hydrolytic stability of compositions according to the invention is significantly improved by the addition of sterically hindered piperidine (i.e. HALS) containing compounds.

Composition A is based on samples of Stabilizer I which are products of technical quality mainly composed of tetrakis-(2,4-di-tert-butyl-phenyl)-biphenylene-diphosphonite (commercially available as SANDOSTAB P-EPQ from SANDOZ). The samples are prepared by melt blending 9 g of Sandostab P-EPQ and 1 g of the component b) as given below in Table 2 at 150° C. in a nitrogen atmosphere. The composition is stirred for 10 minutes for homogenization and then cooled in an ice bath. The resulting glass-like product is then ground into a powder. The hydrolysis test was made under accelerating, severe conditions at 60° and 80% relative humidity. The various samples were exposed to these conditions and analyzed from time to time. Standard HPLC analysis of both, formed 2,4-di-tert-butylphenol, which is a measure of residual Stabilizer I as 82% DTBP would mean that all the SANDOSTAB P-EPQ has been decomposed.

TABLE 2

Hydrolytic stability of Stabilizer I in Compositions A

| Sample Composition A | Content of DTBP after exposure at 60° C., 80% r.h. | | |
|---|---|---|---|
| | after 1 day | after 2 days | after 3 days |
| a) without HALS compound | 34% | 52% | 61% |
| b) plus 1% Sanduvor 3052 | 8% | 10% | 40% |
| c) plus 1% Tinuvin 622 | 18% | 33% | 55% |
| d) plus 1% Chimassorb 944 | 15% | 41% | 57% | r.h = relative humidity;

Sanduvor 3052 is a compound of the formula

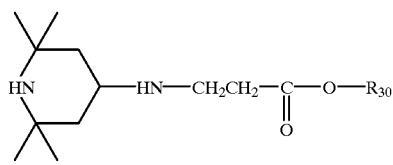

where $R_{30}$ is $C_{12\text{-}14}$alkyl (e.g. a mixture of $C_{12}H_{25}$ and $C_{14}H_{29}$);

Tinuvin 622 is a compound of the formula

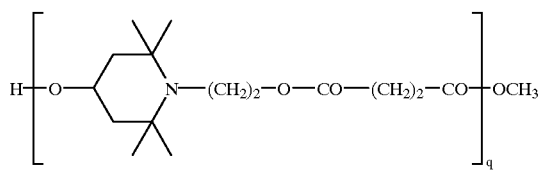

where q=3–20.

Chimassorb 944 is a compound of the formula

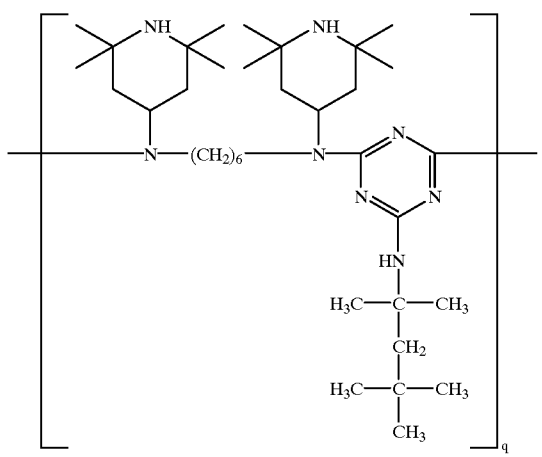

where q is 3–20.

EXAMPLE 2

To a solution of 93 g tetrakis-(2,4-di-tert-butyl-phenyl)-biphenylene-diphosphonite (commercially available as SANDOSTAB P-EPQ from SANDOZ LTD.) in 250 g of chlorobenzene, 7 g of micronized [i.e. particle size less than 1 μm (on average)] zinc oxide are added and homogenized by stirring. The solvent is removed under vacuum and the resulting melt is poured out, cooled and milled. It results in 100 g of an "off"-white powder (composition A).

EXAMPLE 3

The solvent of a solution of 93 g. tetrakis-(2,4-di-tert-butyl-phenyl)-biphenylene-diphosphonite (commercially available as SANDOSTAB P-EPQ from SANDOZ LTD.) in 250 g of chlorobenzene, is removed in vacuum and to the resulting melt at 120–150° C., 7 g of micronized [i.e. particle size less than 1 μm (on average)] zinc oxide are added and homogenized by stirring. The resulting melt is poured out, cooled and milled. It results in 100 g of an "off"-white powder (composition A).

EXAMPLE 4

93 g. tetrakis-(2,4-di-tert-butyl-phenyl)-biphenylene-diphosphonite (commercially available as SANDOSTAB P-EPQ from SANDOZ LTD.) and 7 g of micronized [i.e. particle size less than 1 μm (on average)] zinc oxide are mixed in a Braun mixer to result in 100 g of an "off"-white homogeneous powder (composition A).

The resulting stabilizer I obtained from Examples 2 to 4 is identical so far as chemical and physical properties are concerned.

EXAMPLE 5

Compositions A are blends of SANDOSTAB P-EPQ (Stabilizer I) and zinc oxide as prepared according to Example 2. A hydrolysis test is carried out by inserting a sample into an desiccator and providing a constant humidity by the use of saturated NaCl in water to produce accelerating, severe conditions at 60° C. and 90% relative humidity. The various samples are exposed to these conditions for the time given and analyzed. HPLC analysis of both formed 2,4-di-tert-butylphenol and residual unchanged processing stabilizer, gives consistent results for the degrees of hydrolysis. Alternatively, Compositions A are blends of SANDOSTAB P-EPQ (Stabilizer I) and zinc oxide as prepared according to Example 3 or 4.

Hydrolytic Resistance of Stabilizer I and Composition A at 60° C./ 90% r.h. (accelerated test)

| Sample | Degree of Hydrolysis* (at 60° C., 90% r.h.) after | | | | |
|---|---|---|---|---|---|
| | 0 days | 4 days | 8 days | 14 days | 20 days |
| control | 0% | 85% | n.a. | n.a. | n.a. |
| A (+3% ZnO) | 0.1% | 1.1% | 1.3% | 2.5% | 4.6% |
| A (+5% ZnO) | 0.2% | 0.4% | 1.0% | 2.3% | 3.9% |
| A (+7.5% ZnO) | 0.1% | 0.2% | 0.9% | 1.0% | 1.5% |
| A (+10% ZnO) | 0.2% | 0.4% | 0.9% | 1.6% | 4.5% |

*D.O.H. = 100% - percentage of non-hydrolyzed organophosphorus compound.

The control sample without any hydrolysis guard agent hydrolyses by 50% (half-life period) within ca. 45 hours under the test conditions applied. Prolonged exposure completely destroys the sample within a few days.

The outstanding result obtained with 7.5% micronised ZnO added (as described above) to Stabilizer I is unexpected and corresponds to a significant improvement of the hydrolytic stability by more than one order in magnitude. This surprising finding is of great technical relevance since it has become possible in this way to avoid the various disadvantages described above which have been connected with the use and handling of moisture sensitive organophosphorus stabilizers in technical applications, e.g. as antioxidants/processing stabilizers for polymers.

APPLICATION EXAMPLE

A polymeric composition containing 100.0 parts 3rd generation polypropylene homopolymer 0.05 parts Irganox 1010, tetrakis[methylene-3(3'5-ditert.butyl-4'-hydroxyphenyl) propionate]methane 0.1 parts calcium stearate, and 0.07 parts of a stabiliser Composition A given in the Table below:

are mixed by dry blending and pre-extruding at 210° C. This polymeric composition is then multiply extruded in a Göttfert single screw Extruder (270° C., d-20 mm, l:d=20, 50 min$^{-1}$ compression 1:3) and is granulated, after chilling the polymer melt in a water bath. The melt flow index (ASTM D-1238-70), 230° C., 2.16 kg) and the yellowness index (ASTM D-1925-70, on granules) are determined after the first, third and fifth passage.

TABLE

| Amount of P-EPQ % | Amount of ZnO % | Amount of HALS % | MFI passages | | | YI | | |
|---|---|---|---|---|---|---|---|---|
| | | | 1 | 3 | 5 | 1 | 3 | 5 |
| 97 | 3 | — | 8.22 | 10.2 | 12.6 | −0.2 | 0.7 | 1.8 |
| 95 | 5 | — | 8.25 | 10.0 | 12.7 | −0.4 | 0.9 | 1.9 |
| 92.5 | 7.5 | — | 8.23 | 12.3 | 13.7 | 0.9 | 1.2 | 1.8 |
| 97 | — | 3 | 8.43 | 10.0 | 12.8 | 0.6 | 1.4 | 2.6 |
| 96 | — | 4 | 8.38 | 10.4 | 13.0 | 0.2 | 0.7 | 2.6 |
| 95 | — | 5 | 8.34 | 10.5 | 13.7 | 0.2 | 1.2 | 2.4 |

In the Table above:

HALS is poly{[6-(1,1,3,3-tetramethylbutyl)amino]1,3,5-triazine-2,4diyl][(2,2,6,6-tetramethyl-4-piperidinyl)imino]-1,6-hexanediyl[(2,2,6,6-tetramethyl-4-piperidinyl)imino]}commercially available as Sanduvor 3944;

P-EPQ is tetrakis-(2,4-di-tert-butyl-phenyl)-biphenylenediphosphonite commercially available as the product Sandostab P-EPQ and ZnO is micronised zinc oxide.

What is claimed is:

1. An additive useful as a processing stabilizer for polymers comprising a blend of:

a) one or more phosphonites or phosphites of formulae I to V (hereinafter defined as component a)

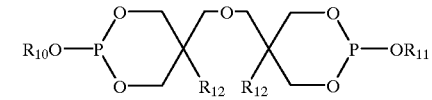

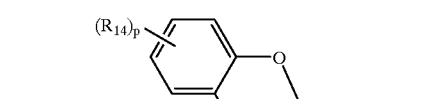

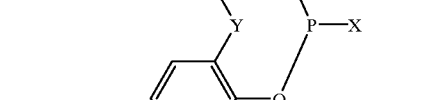

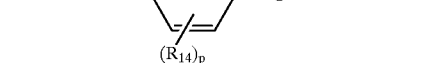

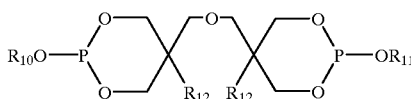

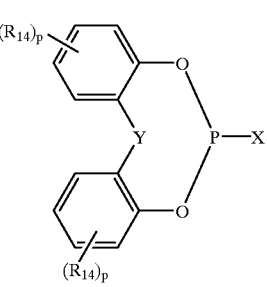

in which m is 0 or 1;

n' is 0 or 1;

p is 0 to 4, each $R_{10}$ and each $R_{11}$, independently, is a group derived from an aliphatic, or alicyclic or aromatic alcohol containing one or two OH groups; whereby the two —OH groups are not positioned to be able to form a P-containing ring; (hereinafter defined as the monovalent significances of $R_{10}$ or $R_{11}$ respectively);

or both groups $R_{10}$ and/or $R_{11}$ form a group derived from an aliphatic, alicyclic or aromatic alcohol containing two or more OH groups in such a position that they can form a cyclic group with a single phosphorus atom (hereinafter defined as the divalent significances of $R_{10}$ or $R_{11}$ respectively);

$R_{12}$ is —OH, CH$_2$OH or C$_{1-4}$alkyl;

each $R_{14}$ independently is selected from C$_{1-22}$alkyl or C$_{7-22}$aralkyl;

X is F or —O—$R_{10}$ where $R_{10}$ is defined; and

Y is —O—, —S—, —CH(R$_{15}$)— or —C$_6$H$_4$—;

where $R_{15}$ is hydrogen or C$_{1-8}$alkyl or COOR$_6$ and R$_6$ is C$_{1-8}$alkyl; with b) micronized zinc oxide.

2. An additive according to claim 1 in which the amount of zinc oxide present is 5–10% based on the weight of component a).

3. A polymeric composition comprising a polymeric material and an additive according to claim 1.

4. A process for stabilising a polymeric composition comprising i) blending a) one or more phosphonites of formulae I to V (hereinafter defined as compound a)

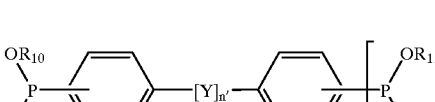

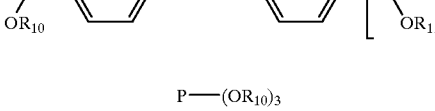

-continued

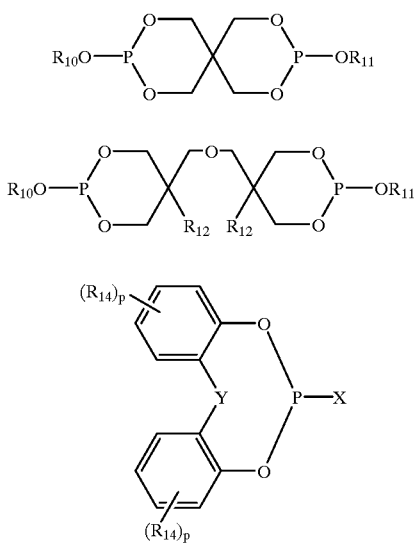

in which
m is 0 or 1;
n is 0 or 1;
p is 0 to 4, preferably 1 to 3 each $R_{10}$ and each $R_{11}$, independently, is a group derived from an aliphatic, or alicyclic or aromatic alcohol containing one or two OH groups; whereby the two —OH groups are not positioned to be able to form a P-containing ring; (hereinafter defined as the monovalent significances of $R_{10}$ or $R_{11}$ respectively);

or both groups $R_{10}$ and/or $R_{11}$ form a group derived from an aliphatic, alicyclic or aromatic alcohol containing two or more OH groups in such a position that they can form a cyclic group with a single phosphorus atom (hereinafter defined as the divalent significances of $R_{10}$ or $R_{11}$ respectively);

$R_{12}$ is —OH, $CH_2OH$ or $C_{1-4}$alkyl;

each $R_{14}$ independently is selected from $C_{1-22}$alkyl or $C_{7-22}$aralkyl;

X is F or —O—$R_{10}$;

Y is —O—, —S—, —CH($R_{15}$)— or —$C_6H_4$—, where $R_{15}$ is hydrogen or $C_{1-8}$alkyl or $COOR_6$ and $R_6$ is $C_{1-8}$alkyl; with b) micronized zinc oxide (hereinafter defined as component b); followed by ii) adding this blend to the polymeric material.

* * * * *